United States Patent
Pohl et al.

(10) Patent No.: US 7,528,283 B2
(45) Date of Patent: May 5, 2009

(54) PROCESS FOR PREPARING DIAMINES AND POLYAMINES FROM THE DIPHENYLMETHANE SERIES

(75) Inventors: Fritz Pohl, Brunsbuttel (DE); Jeffrey Bolton, Dusseldorf (DE); Richard Adamson, Leichlingen (DE); Heinz-Herbert Muller, Krefeld (DE); Rudolf Uchdorf, Shanghai (CN)

(73) Assignee: Bayer MeterialScience AG, Leverkusen (DE)

( * ) Notice: Subject to any disclaimer, the term of this patent is extended or adjusted under 35 U.S.C. 154(b) by 94 days.

(21) Appl. No.: 11/657,147

(22) Filed: Jan. 24, 2007

(65) Prior Publication Data
US 2007/0179316 A1    Aug. 2, 2007

(30) Foreign Application Priority Data
Jan. 28, 2006    (DE) ....................... 10 2006 004 047

(51) Int. Cl.
*C07C 209/78*    (2006.01)

(52) U.S. Cl. .................. 564/331; 564/332; 564/333; 564/334; 564/409

(58) Field of Classification Search ............... None
See application file for complete search history.

(56) References Cited

U.S. PATENT DOCUMENTS

| | | | |
|---|---|---|---|
| 4,792,624 A | 12/1988 | Hatfield, Jr. et al. | 564/333 |
| 5,053,539 A | 10/1991 | Yano et al. | 564/333 |
| 5,196,591 A | 3/1993 | Knöfel et al. | 564/331 |
| 5,286,760 A | 2/1994 | Bolton et al. | 521/160 |
| 5,310,769 A | 5/1994 | König et al. | 521/163 |
| 6,433,219 B1 | 8/2002 | Ströfer et al. | 560/347 |
| 6,649,798 B2 | 11/2003 | Klein et al. | 564/332 |
| 6,831,192 B2 | 12/2004 | Ströfer et al. | 560/347 |
| 7,041,776 B2 | 5/2006 | Koch et al. | 528/269 |
| 2002/0132953 A1 | 9/2002 | Strofer et al. | 528/44 |
| 2003/0023116 A1 | 1/2003 | Klein et al. | 564/404 |
| 2004/0092701 A1 | 5/2004 | Koch et al. | 528/269 |
| 2005/0014975 A1 | 1/2005 | Strofer et al. | 564/330 |

FOREIGN PATENT DOCUMENTS

| | | |
|---|---|---|
| DE | 238 042 A1 | 8/1986 |
| DE | 295 628 A5 | 11/1991 |
| DE | 198 04 918 A1 | 8/1999 |
| EP | 0 031 423 B1 | 6/1984 |
| EP | 1 167 343 B1 | 5/2003 |
| EP | 0 934 922 B1 | 4/2004 |
| GB | 1180795 | 2/1970 |
| JP | 2004-26753 | 1/2004 |

OTHER PUBLICATIONS

Chem. Soc. Rev. 3(2), (month unavailable) 1974, p. 209-230, H.J. Twitchett, "Chemistry of the Production of Organic Isocyanates".
Kirk-Othmer Encycl. Chem. Technol., 3rd Ed. (2), (month unavailable) 1978, p. 338-348, William M. Moore, "Methylenedianiline".

*Primary Examiner*—Brian J Davis
(74) *Attorney, Agent, or Firm*—Noland J. Cheung; N. Denise Brown; John E. Mrozinski, Jr.

(57) ABSTRACT

The invention provides an improved process for preparing diamines and polyamines from the diphenylmethane series by reacting aniline and formaldehyde in the presence of an acid catalyst, the improvement involving the aniline containing less than about 3 wt. % of diamines and polyamines from the diphenylmethane series, based on the weight of the aniline.

18 Claims, No Drawings

PROCESS FOR PREPARING DIAMINES AND POLYAMINES FROM THE DIPHENYLMETHANE SERIES

FIELD OF THE INVENTION

The present invention relates to a process for preparing diamines and polyamines from the diphenylmethane series (MDA) by reacting aniline and formaldehyde in the presence of an acid catalyst, wherein the aniline used contains less than 3 wt. % of MDA, based on the weight of the aniline.

BACKGROUND OF THE INVENTION

Diamines and polyamines from the diphenylmethane series (MDA) are understood to be amines and mixtures of amines of the following type:

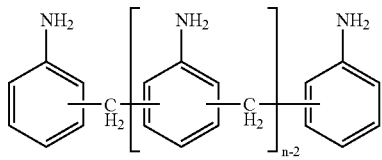

wherein n stands for a natural number $\geq 2$.

The term monomeric MDA (MMDA) for compounds and mixtures of compounds with n=2 and the term polymeric MDA (PMDA) for compounds and mixtures of compounds with n>2 are also conventional. For the sake of simplicity, mixtures of compounds in which compounds with n=2 and n>2 occur side by side are conventionally grouped together under the term MDA (diamines and polyamines from the diphenylmethane series).

The continuous, discontinuous or semi-continuous preparation of diamines and polyamines from the diphenylmethane series is described in numerous publications and patents (for example H. J. Twitchett, *Chem. Soc. Rev.* 3 (2), 209 (1974); M. V. Moore in: *Kirk-Othmer Encycl. Chem. Technol.*, 3rd Ed., New York, 2, 338-348 (1978); EP-A-31 423; EP-B-1 167 343; EP-A-1 403 242; EP 934 922 B1).

In the processes that are employed in industry, MDA is conventionally prepared by reacting aniline and formaldehyde in the presence of acid catalysts, the acid catalyst conventionally being neutralized at the end of the process by addition of a base, the reaction mixture being separated into an organic and an aqueous phase and the organic phase being sent to the final processing stages, such as for example removal of excess aniline by distillation (U.S. Pat. No. 5,310,769; DE-A-198 04 918; JP-A-2004026753).

Common to all of the processes described in the literature for preparing MDA by reacting aniline and formaldehyde in the presence of an acid catalyst is the fact that chromophores are formed during the reaction which discolor the MDA that is produced. During neutralization of the acid catalyst and removal of the aniline that is used in excess in the reaction, these discolorations are not or not adequately reduced or removed, and during the subsequent phosgenation of the MDA to form the corresponding diisocyanates and polyisocyanates and their subsequent processing (separation of the solvent, separation of monomeric MDI), they commonly lead to darkly colored products which in turn result in polyurethane foams having a yellowish discoloration or to other discolored polyurethane (PU) materials. Although the natural color of the diisocyanates and polyisocyanates has no negative influence on the mechanical properties of the polyurethanes that are produced therefrom, light-colored products are preferred because of their good variability in the manufacturer's production process, for example in terms of visibility through thin top coats and colored design possibilities.

There has been no shortage of attempts to reduce the discoloration of MDA.

EP 1 270 544 B1 describes a process for preparing MDA with minimization of the content of undesirable by-products by reacting aniline with formaldehyde in the presence of acid catalysts, characterized in that in a semi-continuous process aniline and optionally acid catalyst are prepared, formaldehyde and optionally acid catalyst are introduced by means of a mixer into a circuit in which aniline, optionally acid and optionally already added formaldehyde are circulated and after introduction of at least 50% of the total amount of formaldehyde to be introduced the reaction mixture is heated to a temperature of greater than 75° C. In particular, minimization of the content of N-methyl MDA is claimed, the reduction of which in MDA according to the teaching of EP 1 270 544 B1 is supposed to lead to a lighter color in a subsequent phosgenation stage to produce a crude MDI.

Improving the color values by reducing the content of N-methyl MDA in the MDA produced, by means of a special introduction of formaldehyde, is also the basis of the following processes.

DD-A-295 628 describes for a discontinuous process adding the formaldehyde in two steps during the condensation stage, the bulk of the formaldehyde being added in the first step at a relatively low temperature and the remaining formaldehyde being added in the second step at the same or a higher temperature.

EP-A-451 442 and DD-A-238 042 disclose for a continuous process adding the formaldehyde in several process steps.

To improve the color values, in addition to minimizing the content of N-methyl MDA, U.S. Pat. No. 5,286,760 also teaches the minimization of the by-products acridan and acridine. U.S. Pat. No. 5,286,760 does not modify the introduction of formaldehyde, however, but rather the rearrangements following the primary reaction of the formaldehyde with aniline. For a continuous MDA production U.S. Pat. No. 5,286,760 describes a partial neutralization of the reaction mixture between the condensation stage of two molecules of aniline and one molecule of formaldehyde and the subsequent rearrangement of the aminobenzylamines formed as intermediates (ABA for short) to form MDA.

U.S. Pat. No. 5,310,769 too intervenes above all in the rearrangements. U.S. Pat. No. 5,310,769 describes a process for preparing polyamines from the diphenylmethane series by condensation of aniline with formaldehyde, subsequent reaction in the presence of an acid catalyst, neutralization of the acid catalyst on completion of the reaction and purification of the resulting mixture of diamines and polyamines by removing the excess aromatic amine by distillation, characterized in that in a preferred variant a) aniline is reacted with formaldehyde in a molar ratio of 1.5:1 to 10:1 at temperatures of between 10 and 150° C., b) after which an acid catalyst is added to the reaction mixture in a molar ratio of aniline to acid catalyst of 2:1 to 100:1 at temperatures of between 10 and 150° C., the water forming in the condensation reaction being separated off either before or after step b), c) then the temperature of the mixture obtained in step b) is increased by at least 40° C. within 15 minutes and it is then heated further to the final temperature between 105 and 200° C. and the temperature held for 10 to 300 minutes following the increase in temperature.

U.S. Pat. No. 5,310,769 teaches that through the special temperature control during the condensation and rearrangement stages a mixture of diamines and polyamines from the diphenylmethane series is obtained whose subsequent phosgenation makes it possible to obtain particularly light-colored polyurethane foams.

Mixtures of diamines and polyamines from the diphenylmethane series whose subsequent phosgenation leads to polyisocyanates having a strongly reduced coloration are also obtained according to U.S. Pat. No. 4,792,624 by the use of a process which is characterized in that a) fast-flowing streams of aqueous aniline hydrochloride and aqueous formaldehyde in a ratio of 1.6 to 8 mol of aniline per mol of formaldehyde are mixed together intensively at the entrance to a tubular type reactor, as a result of which a mixture containing aminobenzylamines is immediately formed, b) the mixture produced according to a) is then passed through a cooled reaction zone in which the content of aminobenzylamines in the mixture increases to at least 30 wt. %, c) the reaction mixture is removed from the cooled reaction zone at the same rate as reaction mixture flows in from step a), d) the reaction mixture from the cooled reaction zone is then passed through a rearrangement zone with temperatures of 60° to 200° C., in which the polyamine from the diphenylmethane series is formed, e) the reaction mixture is removed from the rearrangement zone at the same rate as reaction mixture is fed into the rearrangement zone, f) the reaction mixture from the rearrangement zone is supplied continuously to a neutralization zone in which the acid components are neutralized, then aniline and water are separated off from the reaction mixture, such that an aniline-free polyamine from the diphenylmethane series is obtained, g) the polyamine mixture is removed from step f) at the same rate as reaction mixture is introduced into the neutralization or distillation stage, and h) the bulk of the polyamine mixture obtained is discharged into a storage tank but a partial stream of the polyamine mixture in an amount of 1 to 40 wt. % based on the combined initial weights of the amounts of aniline, aniline hydrochloride and formaldehyde introduced in step a) is returned to step b) and during the ongoing process a) to h) is again passed through steps b) to h).

According to U.S. Pat. No. 4,792,624, to achieve a maximum improvement in color values it is substantial for the excess aniline used in the process to be separated from the MDA before the MDA is added to the benzylamines. Furthermore, according to the teaching of U.S. Pat. No. 4,792,624 the improved coloration is only achieved if the recycled polyamine is added where aminobenzylamines are present and not at the stage in which the aniline and formaldehyde first react.

Common to all of the processes cited and described in the literature for preparing diamines and polyamines from the diphenylmethane series by reacting aniline with formalin in the presence of acid catalysts is the fact that they achieve improvements in the coloration of the mixtures of diamines and polyamines that are formed or of the isocyanates and polyurethanes produced from them by modifying individual process parameters, e.g. the addition of components, the concentration of acid catalyst, the temperature control or the product composition during the rearrangements. There is nevertheless still a need for new processes with still greater color improvements.

SUMMARY OF THE INVENTION

Surprisingly, this color improvement is achieved by using an aniline containing less than 3 wt. %, preferably 0.001 to 3 wt. %, particularly preferably 0.01 to 1 wt. %, of diamines and polyamines from the diphenylmethane series, based on the weight of the aniline used, in the preparation of diamines and polyamines from the diphenylmethane series by reacting aniline and formaldehyde in the presence of acid catalysts.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

The present invention provides an improved process for preparing diamines and polyamines from the diphenylmethane series by reacting aniline and formaldehyde in the presence of an acid catalyst, the improvement involving the aniline containing preferably less than 3 wt. %, more preferably 0.001 to 3 wt. %, most preferably 0.01 to 1 wt. %, of diamines and polyamines from the diphenylmethane series, based on the weight of the aniline.

The use according to the invention of aniline containing preferably less than 3 wt. %, more preferably 0.001 to 3 wt. %, most preferably 0.01 to 1 wt. %, of diamines and polyamines from the diphenylmethane series is of particular importance insofar as the reaction of aniline with formaldehyde in the presence of acid catalysts to establish the desired content of diamines and to ensure the manageability of the reaction mixtures is always performed with an aniline excess. This aniline excess has to be separated off during processing of the mixture of diamines and polyamines and returned to the reaction stages of the process to preserve the external mass balance.

Separation of the aniline excess from the reaction mixture obtained by reacting aniline and formaldehyde is conventionally performed by distillation, the water still adhering to the polyamine mixture likewise being separated off. A largely MDA-free and water-free aniline can be obtained here only with considerable effort.

Surprisingly it was also found that this effort can largely be dispensed with if the waste water accumulating during the reaction of aniline with formalin in the presence of acid catalysts with subsequent neutralization and separation and processing of the organic phase is not extracted, as is conventional in the art (See, e.g., JP 2004026753), with an additionally used hydrophobic solvent but instead, to purify the waste water, the waste water is mixed with the condensates from the aniline separation, which undergo no further processing, and a phase separation is then performed. The organic phase that is obtained can be returned to the synthesis stages of the process as described above as an MDA-loaded aniline to preserve the advantageously low MDA contents, optionally with addition of freshly used aniline.

The invention provides a process for preparing diamines and polyamines from the diphenylmethane series (MDA), wherein a) aniline preferably containing less than 3 wt. %, more preferably 0.001 to 3 wt. %, most preferably 0.01 to 1 wt. %, of diamines and polyamines from the diphenylmethane series, based on the weight of the aniline, is reacted with formaldehyde in the presence of an acid catalyst to form a reaction mixture containing diamines and polyamines, b) the reaction mixture containing diamines and polyamines is neutralized, c) the neutralized reaction mixture containing diamines and polyamines is separated into an organic phase containing diamines and polyamines and an aqueous phase, d) the organic phase is optionally washed with water, e) excess aniline is removed from the organic phase by distillation, f) all or part of the waste water and condensates accumulating in steps a) to e) are combined, wherein at least the waste water and condensates obtained in steps c) and e) are combined at least in part, and wherein a mixture containing water, diamines and polyamines, aniline and salts of the catalyst used in step a) is obtained, g) the mixture obtained in step f) undergoes a phase separation wherein an aniline containing diamines and polyamines is obtained, and h) at least part of the aniline containing diamines and polyamines obtained in the phase separation is then returned to the reaction in step a).

Part of the aniline containing diamines and polyamines obtained in the phase separation in step g) is preferably additionally introduced to one of steps b) to e).

The extracted waste water obtained in step g) preferably undergoes an extraction with aniline, preferably with freshly used aniline. The extracts obtained in this process are further preferably added to the mixture obtained in step f).

The improvement of aniline preferably containing MDA in contents of less than 3 wt. %, more preferably 0.001 to 3 wt. %, most preferably 0.01 to 1 wt. % of MDA, based on the weight of the aniline, to produce mixtures of diamines and polyamines having low color values, can take place in all known processes for preparing MDA from aniline and formaldehyde in the presence of acid catalysts. It should be noted that only the specified limits of the NDA content in the aniline used in the apparatus for the single-stage or multi-stage reaction of aniline with formaldehyde are complied with and that local overconcentrations are avoided.

The aniline used in step a) may preferably prepared by combining at least a partial amount of the aniline obtained in step g) containing diamines and polyamines with aniline deriving from other sources, preferably fresh aniline. The aniline used preferably contains less than 3 wt. %, more preferably 0.001 to 3 wt. %, most preferably 0.01 to 1 wt. %, of MDA. Any excesses of the aniline obtained in step g) containing diamines and polyamines are preferably fed to the stages of neutralization and/or processing of the mixtures of diamines and polyamines (steps b) to e)).

This processing mode firstly ensures the low content of diamines and polyamines in the aniline used in the reaction in step a) that is necessary for preparing light-colored mixtures of diamines and polyamines from the diphenylmethane series or the isocyanates and polyurethanes produced therefrom. Secondly this processing mode advantageously minimizes the effort needed to process the polyamine mixtures in step e) and the use of energy needed to process the extracts obtained in step g). This is because the preparation of diamines and polyamines from the diphenylmethane series takes place in industry on such a large scale that even small economic improvements of such important large-scale processes are of great economic interest.

The aniline containing MDA in contents of preferably less than 3 wt. %, more preferably 0.001 to 3 wt. %, most preferably 0.01 to 1 wt. %, is preferably first reacted in step a) with formaldehyde in a molar ratio of preferably 1.6:1 to 10:1, more preferably between 1.6:1 and 4.0:1, and at a temperature of preferably between 10 and 150° C., more preferably between 75 and 110° C. Aniline used denotes here the aniline containing diamines and polyamines and optionally other secondary components.

An acid catalyst is preferably added to the reaction mixture in a molar ratio of aniline to acid catalyst of preferably 2:1 to 100:1 (corresponding to a degree of protonation of aniline of 50 to 1%), more preferably 4:1 to 20:1, at a temperature of preferably 10 to 150° C., more preferably 35 to 75° C. Hydrochloric acid is preferably used as the acid catalyst.

The water produced in the condensation of the formaldehyde with the aniline and optionally introduced with the formaldehyde is preferably separated off either in whole or in part before the catalyst addition (e.g. by phase separation) or afterwards (e.g. by evaporative cooling and discharge of the condensates obtained therein).

The reaction mixture is preferably heated to temperatures of between 100 and 180° C., more preferably between 130 and 160° C., and after reaching the final temperature is held at this temperature for 5 to 300 minutes.

In step b) the reaction mixture containing MDA is neutralized, optionally with addition of water and/or aniline. The neutralization preferably occurs with sodium hydroxide solution.

In step c) the neutralized reaction mixture containing MDA is separated into an organic phase containing MDA and an aqueous phase. This can be supported by the addition of aniline and/or water. If the phase separation is supported by the addition of aniline and/or water, their addition preferably takes place with intensive mixing in the neutralization stage. This mixing can take place in mixing sections with static mixers, in stirred-tank reactors or series of stirred-tank reactors or in a combination of mixing sections and stirred-tank reactors. The neutralized reaction mixture diluted through the addition of aniline and/or water is preferably supplied to an apparatus which because of its configuration and/or internals is suitable in particular for separation into an organic phase containing MDA and an aqueous phase. Florentine flasks having as internals plate assemblies supporting the coalescence of the two phases may preferably be used.

In step d) the organic phase containing MDA is optionally washed, preferably at temperatures of between 50 and 150° C., more preferably between 80 and 110° C., with water in a ratio of water to organic phase of 0.05 to 2:1.

The organic phase obtained in step c), optionally after washing in step d), is freed from aniline in step e) in a distillation, wherein a purified MDA and a condensate containing aniline and water are obtained.

The waste water obtained in steps a) to e), as the aqueous phase from step c), the washing water from step d) and the condensate from step e) and optionally other process water such as for example other condensed vapors or aqueous phases obtained in step a), are combined in part or in whole in step f). At least part, preferably at least 50%, of at least the waste water and condensates obtained in steps c) and e) are combined. A mixture is obtained which preferably contains water and 0.001 to 5 wt. % of MDA, 0.5 to 60 wt. % of aniline and 1 to 25 wt. % of salts of the acid catalyst used in step a), based in each case on the weight of the mixture.

The mixture obtained in step f) undergoes a phase separation in step g), preferably at a temperature of between 30 and 120° C., more preferably between 70 and 110° C., wherein an aniline containing diamines and polyamines is obtained.

In a further step of extraction with aniline, preferably with freshly used aniline, preferably at a temperature of between 30 and 120° C., more preferably between 70 and 110° C., the waste water obtained in step g) can optionally be extracted with aniline in the weight ratio of aniline to waste water of preferably 0.05 to 1:1, more preferably 0.1 to 0.3:1, the extracts advantageously being fed to the mixture prepared in step f). This extraction preferably takes place in multiple stages and counter currently. Aniline is preferably used as the sole extractant.

The extraction with freshly used aniline is advantageously supported by the mixing in step f) (involving an extraction) of the waste water and the condensates from the distillative deanilination performed in step e) and the extraction performed in step g). Very small feedstocks of fresh aniline are thus needed for extraction. On account of the freedom of the condensates from phenol, smaller phenol loads are obtained in the extracted waste water.

The removal of aniline from the extracted waste water by distillation is advantageous. Aniline forms a low-boiling azeotrope with water, so the removal by distillation can be performed under an easily managed partial vacuum at temperatures of less than 100° C., and waste heat can advantageously be used as energy in the recovery of aniline by distillation.

The condensates obtained in the distillative removal of aniline from the extracted waste water contain a high proportion of water. The condensates can therefore advantageously be used in whole or in part as diluting water in the neutralization in step b) and as washing water in step d), particularly preferably first as washing water in step d), then as diluting water in the neutralization in step b). A large supply of washing agent is possible in this way without increasing the amount of waste water produced by the process.

If during the distillative removal of aniline from the extracted waste water the vapors are condensed in a multi-stage process, a fraction containing methanol and other low-boiling components in high concentrations can advantageously be produced. The methanol level in the process stages is firstly advantageously lowered as a result, and this fraction can secondly advantageously be used as a fuel substitute.

In step h) all or part of the aniline containing diamines and polyarmines obtained from the phase separation in step g) is finally returned to step a). The recycled aniline is preferably used in the reaction in step a) with no further processing. A further part is optionally used in one of the process steps b) to e).

The improved process according to the invention is characterized first of all by a particularly simple management of the aniline-containing streams accumulating in the extractive processing of its waste water and condensates. Furthermore, the polyamines prepared by the process according to the invention have low contents of chromophores and can advantageously be converted into isocyanates having only slight coloration and into light-colored polyurethane products. The phosgenation of the polyamines and the isolation of the polyisocyanates produced in that process and their conversion into polyurethane products can be performed by the known industrial processes.

Novel and substantial to the process according to the invention is the fact that an aniline which contains preferably less than 3 wt. %, more preferably 0.001 to 3 wt. %, particularly preferably 0.01 to 1 wt. %, of diamines and polyamines from the diphenylmethane series, based on the weight of the aniline used, is used in the reaction of aniline and formaldehyde. Aniline used denotes here the aniline containing diamines and polyamines and optionally other by-products. Through the low content of diamines and polyamines in the aniline that is used, improved color values are obtained for the diamines and polyamines and for the diisocyanates and polyisocyanates or polyurethanes produced therefrom.

Novel and substantial to the preferred process according to the invention is further the fact that the extraction with aniline takes place after the phase separation of the neutralized reaction mixture containing MDA, wherein only the extraction of the aqueous phase is performed with aniline and to that end it is predominantly the aniline-containing condensates from the distillative removal of aniline obtained in step e) that are used as the extractant in step g). This is because the phase separation in step g) actually takes place with simultaneous extraction of the aqueous phase by the aniline contained in the highly aniline-containing condensates (organic phase). The reaction mixture still containing both phases or the organic phase obtained after phase separation is not extracted with aniline in the process according to the invention. In contrast to the art, the use and processing of an additional hydrophobic solvent are dispensed with through the separation of the waste water and the use of the condensates, and only extremely small amounts—if any—of freshly used aniline are needed for processing the waste water.

The coloration of the diisocyanates and polyisocyanates can be characterized by two absorption maxima in the visible UV range at 430 and 520 nm. Based on appropriate experience, the coloration of the polyurethane products produced from the diisocyanates and polyisocyanates from the diphenylmethane series can be predicted from these values. The value at 430 nm corresponds to a yellow-brown, the value at 520 nm to a grey coloration of the polyurethane products produced from the diisocyanates and polyisocyanates. Lower absorption values in the diisocyanates and polyisocyanates correspond to lesser or lighter coloration of the polyurethane products produced from these diisocyanates and polyisocyanates.

The processes according to the invention are described in more detail by reference to the examples below:

EXAMPLES

Example 1

Example with MDA-free technical aniline (according to the invention)

150 ml of aniline from 559 g of technical aniline (6.0 mol) not previously used in the MDA process were placed in an inerted flask and heated to 80° C. with stirring, and the remaining aniline together with 268 g of a 32 wt. % formalin solution (2.86 mol) was steadily added dropwise within 20 minutes.

On completion of the addition the reaction mixture was stirred for a further 5 minutes at 80° C. transferred with exclusion of air into an inerted Florentine flask in which after a separation time of 5 minutes the organic phase was separated off.

150 ml of the separated organic phase were placed in an inerted flask, then the rest of the organic phase together with 183 g of a 30 wt. % hydrochloric acid (1.5 mol) was steadily added dropwise within 30 minutes with stirring and the temperature held at 35° C. by external cooling.

On completion of the addition of the components, the reaction mixture was held at 35° C. for a further 30 minutes with stirring, heated within 10 minutes to 60° C., stirred at this temperature in turn for 30 minutes, heated to reflux temperature within 30 minutes and lightly refluxed for a further 10 hours to complete the reactions.

To neutralize the acid catalyst, 144 g of a 50 wt. % sodium hydroxide solution (1.8 mol) were added to the hot reaction mixture within 5 minutes, and 100 ml of boiling distilled water were added to the reaction mixture to improve the phase separation and the mixture was held under light reflux for a further 15 minutes.

The organic phase was separated off, washed twice with water with the addition in each case of 600 ml of boiling distilled water, held for 5 minutes under light reflux and transferred after washing to a distillation apparatus, where it was freed from adhering low-boiling components such as water and excess aniline at 10 mbar until the start of binuclear distillation.

A polyamine mixture characterized by the following contents was obtained:

| | |
|---|---|
| 4,4'-MDA | 54.40 wt. % |
| 2,4'-MDA | 3.27 wt. % |
| 2,2'-MDA | 0.074 wt. % |
| N-methyl MDA | 0.39 wt. % |
| total binuclear MDA | 58.13 wt. % |
| total trinuclear MDA | 22.92 wt. % |
| total tetranuclear MDA | 10.20 wt. % |

In an inerted flask of a laboratory phosgenating apparatus, 310 ml of dried monochlorobenzene were introduced and cooled to 0° C., 105 g of phosgene were fed into the cooled monochlorobenzene and condensed, a 55-degree solution of 50 g of the polyamine mixture—prepared as described above—in 255 ml of monochlorobenzene were added within 10 seconds with intensive stirring, during which process the reaction mixture heated up to approx. 50° C.

The suspension produced was heated to 100° C. within 45 minutes with intensive stirring and further phosgene addition at a rate of 60 g/h, heated to reflux (approx. 135° C.) within a further 10 minutes and refluxed until the clear point was reached.

The phosgene feed was adjusted and the clear reaction mixture transferred to a distillation apparatus, where with an overhead vacuum of approx. 12 mbar it was freed from excess phosgene and the solvent, it was heated under medium vacuum (2-3 mbar) for 15 minutes at a bottom temperature of approx. 195° C. and then cooled under nitrogen blanketing.

An MDI mixture is obtained which is characterized by

| | |
|---|---|
| NCO content (%) | 31.46 |
| viscosity/25° C. (mPas) | 77 |
| Cl, total (%) | 0.16 |
| $E_{430}$ | $0.174^{1)}$ |
| $E_{520}$ | $0.026^{1)}$ |

[1)] 1.0 g of the isocyanate obtained was dissolved in chlorobenzene and diluted with chlorobenzene to 50 ml. The absorbance of the solution thus obtained was measured with a Dr Lange LICO 300 photometer at the two wavelengths 430 nm and 520 nm.

Example 2

Reaction with technical aniline to which 2.5 wt. % of 4,4'-MDA has been added (according to the invention)

The reaction of technical aniline previously doped with 2.5 wt. % of 4,4'-MDA to form the polyamine mixtures and the reaction of the polyamine mixtures to form the corresponding isocyanates took place in an analogous manner to Example 1, under the reaction conditions specified therein.

A polyamine mixture characterized by the following contents was obtained:

| | |
|---|---|
| 4,4'-MDA | 53.70 wt. % |
| 2,4'-MDA | 2.95 wt. % |
| 2,2'-MDA | 0.054 wt. % |
| N-methyl MDA | 0.41 wt. % |
| total binuclear MDA | 57.11 wt. % |
| total trinuclear MDA | 23.20 wt. % |
| total tetranuclear MDA | 10.60 wt. % |

An MDI mixture was obtained from the polyamine mixture which was characterized by

| | |
|---|---|
| NCO content (%) | 31.54 |
| viscosity/25° C. (mPas) | 81 |
| Cl, total (%) | 0.19 |
| $E_{430}$ | $0.212^{1)}$ |
| $E_{520}$ | $0.037^{1)}$ |

Example 3

Reaction with technical Aniline to which 5.0 wt. % of 4,4'-MDA has been added (not according to the invention)

The reaction of technical aniline previously doped with 5.0 wt. % of 4,4'-MDA to form the polyamine mixtures and the reaction of the polyamine mixtures to form the corresponding isocyanates took place in an analogous manner to Example 1, under the reaction conditions specified therein.

A polyamine mixture characterized by the following contents was obtained:

| | |
|---|---|
| 4,4'-MDA | 52.10 wt. % |
| 2,4'-MDA | 2.64 wt. % |
| 2,2'-MDA | 0.045 wt. % |
| N-methyl MDA | 0.41 wt. % |
| total binuclear MDA | 55.20 wt. % |
| total trinuclear MDA | 23.50 wt. % |
| total tetranuclear MDA | 11.20 wt. % |

An MDI mixture was obtained from the polyamine mixture which was characterized by

| | |
|---|---|
| NCO content (%) | 31.50 |
| viscosity/25° C. (mPas) | 89 |
| Cl, total (%) | 0.21 |
| $E_{430}$ | $0.266^{1)}$ |
| $E_{520}$ | $0.051^{1)}$ |

Example 4

Use of condensates from the deanilination stage and freshly used aniline as extractants in a waste water processing stage (according to the invention)

27.4 t/h of a mixture, containing quantitatively waste water and condensates from the stages of a process characterized in that a) aniline and formalin were reacted in the presence of 30 wt. % hydrochloric acid as catalyst, b) the reaction mixture was neutralized with sodium hydroxide solution, c) the organic phase was separated off, d) the organic phase was washed with hot water and e) excess aniline was removed from the organic phase by distillation, the condensates were fed to the collected waste water (all waste water from steps a) to d)) with no further processing, containing 0.25 wt. % of MDA, 25.7% of aniline and 6.3 wt. % of sodium chloride, were heated by a heat exchanger to temperatures >80° C. and in order to be processed were fed to a separation stage (step g)) and then to a two-stage extraction stage operated counter currently with MDA-free aniline as the extractant, wherein before being introduced into the separation stage (phase separation in step g)) the MDA-free aniline supplied at a rate of 1.5 t/n was heated to temperatures >50° C., the freshly used aniline and the aniline leaving the first and second stage of the extraction stage were mixed intensively with the counter currently supplied waste water or the mixture used with an introduction of energy of 0.1 kW/m$^3$ of waste water, separated again in settlers connected downstream from the mixers with average residence times of 20 minutes and at temperatures held at >80°, the extracted waste water was fed to a distillative separation stage to remove its content of dissolved aniline, the entire loaded aniline phases from the separation stage (step g)) were introduced into an aniline feedstock receiver, where they were mixed with freshly supplied aniline, the mixture was returned to the reaction stages of the process as aniline feedstock.

Following the extraction the waste water supplied to the downstream distillative aniline separation stage contained <1 ppm MDA and was likewise free from aminals and aminobenzylamines. Its aniline content of 2.1 wt. % corresponded to the solution equilibrium. Aniline quantities which were fed for waste water processing in addition to the feedstock mixture, together with the extract, formed the organic phase of the separation stage.

The organic phase of the separation stage had MDA contents of 0.78 wt. %. Through the introduction of 10.4 t/h of freshly obtained technical aniline, MDA loads of 0.34% were obtained in the aniline feedstock.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of diamines and polyamines from the diphenylmethane series comprising reacting aniline which contains less than about 3 wt. % of diamines and polyamines from the diphenylmethane series, based on the weight of the aniline, with formaldehyde in the presence of an acid catalyst.

2. The process according to claim 1, wherein a) aniline containing less than about 3 wt. % of diamines and polyamines from the diphenylmethane series, based on the weight of the aniline, is reacted with formaldehyde in the presence of an acid catalyst to form a reaction mixture containing diamines and polyamines, b) the reaction mixture containing diamines and polyamines is neutralized, c) the neutralized reaction mixture containing diamines and polyamines is separated into an organic phase containing diamines and polyamines and an aqueous phase, d) the organic phase is optionally washed with water, e) excess aniline is removed from the organic phase by distillation, f) part or all of the waste water and condensates accumulating in steps a) to e) are combined, wherein at least the waste water and condensates obtained in steps c) and e) are combined at least in part, and wherein a mixture containing water, diamines and polyamines, aniline and salts of the catalyst used in step a) is obtained, g) the mixture obtained in step f) undergoes a phase separation wherein an aniline containing diamines and polyamines is obtained, and h) at least part of the aniline containing diamines and polyamines obtained in the phase separation is returned to the reaction in step a).

3. The process according to claim 2, wherein the aniline contains about 0.001 to about 3 wt. % of diamines and polyamines from the diphenylmethane series, based on the weight of the aniline.

4. The process according to claim 2, wherein the aniline contains about 0.01 to about 1 wt. % of diamines and polyamines from the diphenylmethane series, based on the weight of the aniline.

5. The process according to claim 2, wherein in step f) a mixture containing water and about 0.001 to about 5 wt. % of MDA, about 0.5 to about 60 wt. % of aniline and about 1 to about 25 wt. % of salts of the acid catalyst in step a), based in each case on the weight of the mixture, is obtained.

6. The process according to claim 2, wherein the phase separation in step g) takes place at a temperature of between about 30 and about 120° C.

7. The process according to claim 2, wherein the phase separation in step g) takes place at a temperature of between about 70 and about 110° C.

8. The process according to claim 2, wherein in a further extraction stage at a temperature of between about 30 and about 120° C., the extracted waste water obtained in step g) is extracted with aniline in the weight ratio of aniline to waste water of about 0.05 to about 1:1, and the extracts obtained are added to the mixture obtained in step f).

9. The process according to claim 8, wherein the temperature is between about 70 and about 110° C., and the weight ratio of aniline to waste water is from about 0.1 to about 0.3:1.

10. The process according to claim 8, wherein in the extraction stage the waste water is extracted in a multi-stage process.

11. The process according to claim 8, wherein in the extraction stage the waste water is extracted counter currently.

12. The process according to claim 8, wherein part of the aniline containing MDA obtained in the extraction stage is returned to one or more of steps a) to e).

13. The process according to claim 2, wherein aniline is removed by distillation from the waste water obtained in the phase separation in step g) and wherein at least part of the extracted aniline, in the form of its condensed vapors, is returned to the neutralization stage in step b) and/or to the washing stage in step d).

14. The process according to claim 13, wherein the vapors produced in the distillative separation of the aniline are condensed in a multi-stage process, wherein a fraction containing about 20 to about 95 wt. % of methanol is obtained.

15. The process according to claim 13, wherein the vapors produced in the distillative separation of the aniline are condensed in a multi-stage process, wherein a fraction containing about 60 to about 80 wt. % of methanol is obtained.

16. The process according to claim 12, wherein aniline is removed by distillation from the waste water obtained in the extraction stage and wherein at least part of the extracted aniline, in the form of its condensed vapors, is returned to the neutralization stage in step b) and/or to the washing stage in step d).

17. The process according to claim 16, wherein the vapors produced in the distillative separation of the aniline are condensed in a multi-stage process, wherein a fraction containing about 20 to about 95 wt. % of methanol is obtained.

18. The process according to claim 16, wherein the vapors produced in the distillative separation of the aniline are condensed in a multi-stage process, wherein a fraction containing about 60 to about 80 wt. % of methanol is obtained.

* * * * *